United States Patent [19]

Saint Felix et al.

[11] Patent Number: 5,287,274

[45] Date of Patent: Feb. 15, 1994

[54] METHOD FOR ACQUISITION OF RADIOLOGICAL DATA IN MULTIPLE ORTHOGONAL ORIENTATIONS USING A 2D DETECTOR RELATING TO A BODY IRRADIATED WITH X-RAYS AND FOR RECONSTRUCTION OF STRUCTURES CORRESPONDING TO SAID BODY USING AN ALGEBRAIC ALGORITHM

[75] Inventors: Didier Saint Felix, Boulogne; Yves Trousset, Paris; Catherine Picard, Boulogne; Anne Rougee, Fontenay aux Roses, all of France

[73] Assignee: General Electric CGR SA, Issy Les Moulineaux, France

[21] Appl. No.: 493,818

[22] Filed: Mar. 15, 1990

[30] Foreign Application Priority Data

Mar. 20, 1989 [FR] France ................. 89 03606

[51] Int. Cl.⁵ .................................... G06F 15/00
[52] U.S. Cl. .................................... 364/413.15
[58] Field of Search .......... 364/413.15, 413.13, 364/413.14, 413.16, 413.19; 250/445 T

[56] References Cited

U.S. PATENT DOCUMENTS

| | | | |
|---|---|---|---|
| 4,128,877 | 12/1978 | Katz | 364/414 |
| 4,145,614 | 3/1979 | Kowalski | 250/445 |
| 4,504,909 | 3/1985 | Acharya et al. | 364/413.15 |
| 4,751,643 | 6/1988 | Lorensen et al. | 364/413.13 |
| 4,791,567 | 12/1988 | Cline et al. | 364/413.13 |
| 4,821,213 | 4/1989 | Cline et al. | 364/413.13 |
| 4,897,788 | 1/1990 | King | 364/413.15 |
| 4,914,588 | 4/1990 | Schittenhelm | 364/413.14 |
| 4,952,922 | 8/1990 | Griffin et al. | 364/522 X |
| 4,989,142 | 1/1991 | Crawford | 364/413.15 |
| 4,992,941 | 2/1991 | Bruening et al. | 364/413.15 |

FOREIGN PATENT DOCUMENTS 2368058 5/1978 France.

OTHER PUBLICATIONS

IEEE Transactions on Nuclear Science, vol. NS-25, No. 5, Oct. 1978, pp. 1135–1143, M. Schlindwein, "Iterative Three-Dimensional Reconstruction from Twin-Cone Beam Projections".

Primary Examiner—Roy N. Envall, Jr.
Attorney, Agent, or Firm—Nilles & Nilles

[57] ABSTRACT

In voludensitometry and in cases in which it is necessary to acquire only a small number of views, the artifact ratio resulting from reconstructions is reduced. There is acquired at least one view of the object to be reconstructed, the principal direction of irradiation of which is oriented substantially at right angles to a plane formed by or containing the other directions of irradiation corresponding to the other views.

13 Claims, 2 Drawing Sheets

METHOD FOR ACQUISITION OF RADIOLOGICAL DATA IN MULTIPLE ORTHOGONAL ORIENTATIONS USING A 2D DETECTOR RELATING TO A BODY IRRADIATED WITH X-RAYS AND FOR RECONSTRUCTION OF STRUCTURES CORRESPONDING TO SAID BODY USING AN ALGEBRAIC ALGORITHM

BACKGROUND OF THE INVENTION

1. Field of the Invention

The present invention relates to a method for acquisition of radiological data relating to a body irradiated with x-rays and for reconstruction of structures corresponding to said body. Reconstruction of structures is aimed at the representation of images of cross-sections, or images of views, of these structures. The method is essentially concerned with the acquisition of radiological data detected by a two-dimensional detector placed opposite to the x-ray transmitter. In contrast to conventional tomodensitometers, the x-radiation in this case irradiates the body in volume and the absorption of this radiation in the body can be measured at the same time for the entire volume of the body and not only in a slice of said volume. The object of acquisitions of this type is clearly to accelerate the stage of measurement of the x-ray absorption phenomenon throughout the entire body.

2. Description of the Prior Art

This mode of acquisition is already known. For example, it was presented by Pierre Grangeat at the second image symposium of the "International Week of the Electronic Image" held at Nice in Apr., 1986. As opposed to tomodensitometry, one accordingly refers to voludensitometry, and a basic system for reconstructing the structures under study is as follows. The system comprises an x-ray point source and the radiation flux has a conical geometry. This source is placed opposite to a body to be examined. A two-dimensional detector is placed on the other side of the body with respect to the source, substantially at right angles to a principal direction of the radiation. This two-dimensional detector is capable of acquiring radiological data which can be digitized.

By causing the acquisition unit comprising the source and the two-dimensional detector to rotate about the body, the irradiation can be reiterated and a set of acquisitions can be obtained. By means of a reconstruction algorithm, it is then possible to distribute digital data over a spatial square grid, these data being representative of a reconstruction of the structure of the body which is subjected to examination. The reconstruction algorithms employed in this type of investigation essentially involves utilization of the 3D Radon transform and its inversion formula. In other words, by reducing the acquisition stage to a few second by means of a system of this type and by employing an appropriate reconstruction algorithm, the desired result is achieved.

The reconstruction algorithms thus mentioned require that the path of travel of the x-ray source and the corresponding path of the 2D detector should be circular with respect to the body to be examined. Since the conical geometry of the radiation makes it impossible to resolve the reconstruction problem into a superposition of two-dimensional reconstructions in parallel cross-sections perpendicular to the axis of rotation of the unit, it is found necessary to develop algorithms based on approximate calculations of the 3D Radon transform and of its inversion.

The use of approximations leads to reconstruction artifacts, with the result that, when it is thus desired to visualize the reconstructed object by selecting cross-sections of this latter or by displaying it directly, these artifacts appear in the images shown. These images cannot readily be processed.

In another approach, the reconstruction is effected by simulating the reconstructed structure, by mathematically projecting the simulation of this structure in accordance with a direction of irradiation, and by comparing the image in simulated projection directly with the measurements resulting from the irradiation. In fact this comparison is made, not for a single direction of irradiation but for all directions of irradiation really carried out. Thus a projection of the simulated structure corresponds to each direction of acquisition. From this comparison is deduced a modification of the simulated model of the structure under study. In a following iteration, the modified simulated model is then projected as before, its projection is again compared with the acquisitions really made, and so on until the comparisons show that the modified simulated model is sufficiently close to the structure which has really been irradiated. These methods of reconstruction by estimation and simulation involving the use of so-called algebraic reconstruction algorithms are wholly suitable when the acquisition number is small or when the irradiations are badly distributed about the body. The number is small in particular when the examination is an angiography in which the injection of a contrast product is traumatizing and cannot be repeated too often. The irradiations are badly distributed when the geometry of the body to be studied or the means for intervention on said body do not permit correct positioning of the source-detector assembly on the entire periphery of a circle which surrounds the zone of interest of the object.

The object of the invention is to work towards the reconstruction of structures with less artifacts than in the known state of the art, this being achieved in respect of an equal acquisition number and by making use of an algebraic reconstruction algorithm. Quite simply, instead of causing the x-ray source to follow a circular path (with a corresponding path for the 2D detector), it is found preferable in accordance with the invention to distribute the orientations of the principal directions of acquisition in space so that all these orientations cannot be located in the same plane. Preferably, the acquisition number will be a minimum of three. These three orientations of the directions of irradiations will be orthogonal to each other. The avoidance orientations located in the same plane is associated with the use of an algebraic reconstruction algorithm.

SUMMARY OF THE INVENTION

The invention is therefore directed to a method for acquisition of radiological data relating to a body irradiated with x-rays and for reconstruction of structures corresponding to said body in order to display images of said structures, said method being distinguished by the fact that, for the purpose of acquisition, it involves the following steps:

a flux of x-rays is directed to the body by means of a transmitter, said flux being such as to have a principal direction of irradiation, a view relating to a given orientation of the principal direction with respect to the body is detected by means of a two-dimensional detector which is maintained opposite to the transmitter, said view being constituted by a collection of data which are a function of the coordinates of loci on said detector and a function of the attenuation within the body of that portion of the x-rays which terminates at said loci, the preceding stages are reiterated in the case of principal directions having different orientations with respect to the body, these orientations are distributed so that a plane formed by two principal directions or directions parallel to said principal directions intersects at least a third orientation, and that, for the purpose of reconstruction, an algebraic reconstruction algorithm is employed.

DETAILED DESCRIPTION OF THE INVENTION

Figure 1:
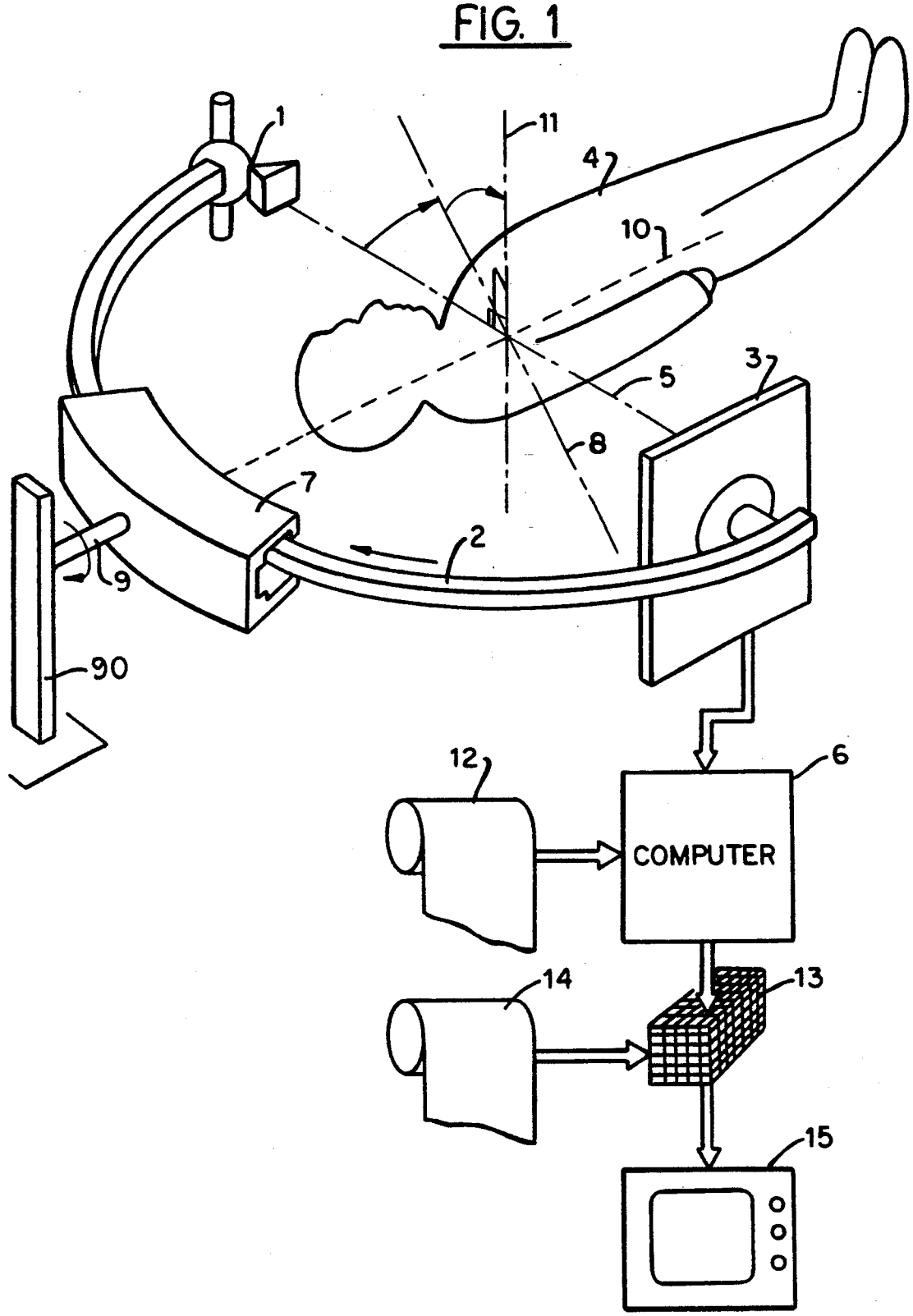
FIG. 1 is a schematic diagram of means employed for carrying out the method in accordance with the invention.

The means employed for carrying out the method in accordance with the invention are illustrated schematically in FIG. 1. These means comprise an x-ray transmitter 1 which is maintained by an arch 2, for example, opposite to a two-dimensional detector 3. The detector 3 is approximately flat and has at its center a normal direction which coincides with a principal direction of irradiation 5. A body 4 to be examined is subjected to irradiation, the principal direction 5 of irradiation being determined with respect to the position of the body 4. For example, when the radiological examination is a study of the heart, this orientation can be lateral from the left to the right of the patient, and can be slightly slantwise from the patient's head to his or her feet. The signal delivered by the detector 3 is processed in a computer 6. In particular, said signal is digitized so that a collection of radiological data corresponds to each irradiation, the values of said data being a function of the locus on the detector from which the measurement originates (these data related to the address on the detector of the locus considered) and being also a function of the attenuation within the body 4 of that part of the x-radiation which has terminated at said locus.

When these results have been obtained, the unit consisting of source 1 and detector 3 is caused to rotate about the patient, for example by displacing the arch 2 in sliding motion within a supporting guide 7. Under these conditions, the principal direction of irradiation 5 moves to a new orientation 8 with respect to the body 4. The orientation 8 is from left to right under the same conditions as before but this time from the patient's feet to his or her head. At this moment, the preceding irradiation-detection stage is reiterated. It may also be conceived in practice that transmission is continuous but that reading of the detector is performed only when the unit has assumed the orientations 5 and 8.

When the unit consisting of source 1 and detector 3 has moved to the orientation 8 and when the corresponding measurements have been acquired at this location, said unit is displaced in rotation about a pivot 9 having a horizontal axis 10 so that the orientation of the principal direction of irradiation is now an orientation 11 located substantially at right angles to the plane formed by the two orientations 5 and 8 aforesaid. To this end, the pivot 9 is attached to the guide 7 and to a pedestal 90. When the source-detector unit is in this orientation 11, a frontal radiograph is acquired.

The radiological data acquired when the unit had the orientations 5, 8 and 11 are stored in the computer memory. A reconstruction program 12 involving the use of an algebraic reconstruction algorithm is then employed. The use of this reconstruction algorithm results in a knowledge of the reconstructed structure 13 corresponding to the body 4. These structures comprise a set of radiological density data distributed over a three-dimensional spatial grid.

By means of methods of visualization 14 of known type, it is possible to extract from the structure 13 images of cross-sections within the body 4 or of visualization of the structures contained in said body. These images are displayed in known manner on a television monitor 15 or on any other display means.

Figures 2A, 2B:
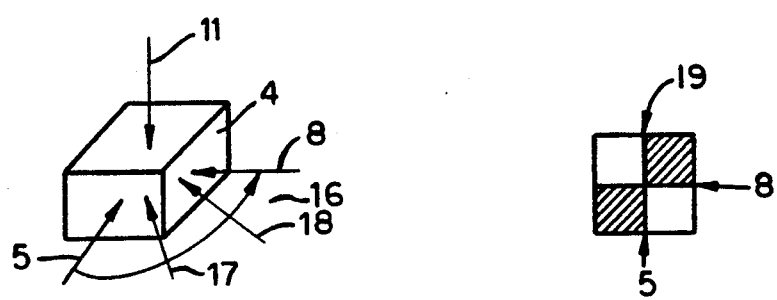
FIGS. 2a and 2b are schematic diagrams showing the justification of the invention.

FIGS. 2a and 2b illustrate the advantage gained by the use of the method of acquisition in accordance with the invention. If scans of a conventional type are employed for a structure 4 to be reconstructed, the orientations of the principal directions of irradiation are distributed over a surface 16 which contains them all. For example, the surface 16 comprises the directions 5, 17, 18 and 8. It is apparent that, if these directions are contained only in a plane 16, they lead to uncertainties in regard to the position of details within the body 4, especially if the of irradiations is small.

On the other hand uncertainties can be definitely removed if rad data are acquired at least once whilst the source-detector unit is in a direction 11 at right angles to the plane 16.

For example, as shown in FIG. 2b, irrespective of the irradiation orientation 5 or 8, the detector placed opposite to the irradiated structure 19 will be confronted with an ambiguity of localization of loci having a high x-ray absorption density with respect to others which have a low density. In fact, in both cases (5 and 8), the results of detection are comparable and do not make it possible to discriminate the loci of the structure 19 in which the density is low. In practice, these uncertainties are partly removed by making a large number of measurements, which is not possible in all cases as has been seen earlier. Removal of ambiguity is partial since it always rests on the value of the angular difference between the orientations. Better discrimination is achieved as this angular difference is greater. In the present invention, while retaining a limited number of irradiations, the ambiguities can be reduced simply by orienting at least one of the irradiations (11) substantially at right angles to the plane 16 formed by the distribution of the other irradiations.

Figure 3:
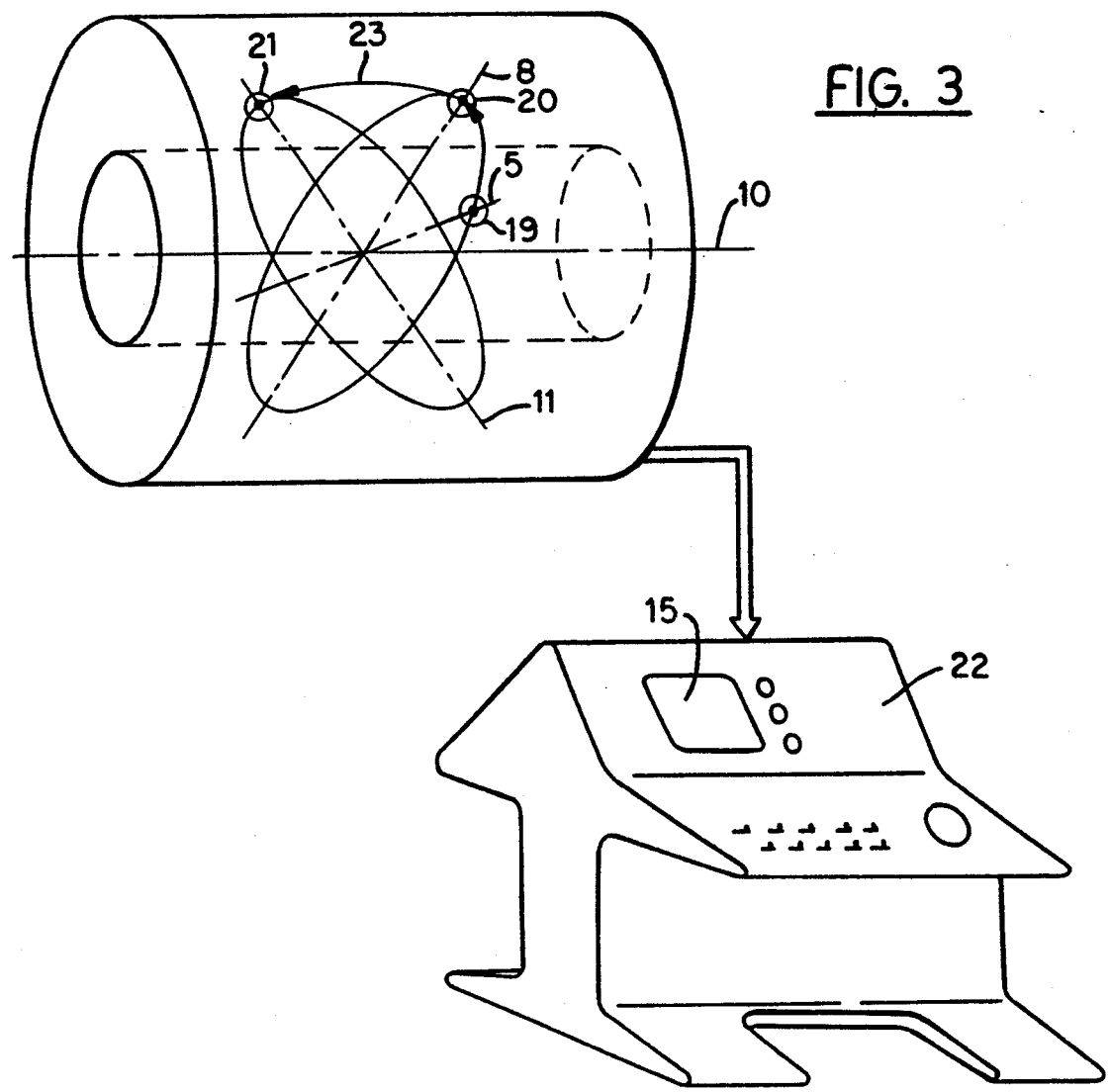
FIG. 3 shows one example of implementation of the invention in a tomodensitometer of conventional type.

FIG. 3 shows a tomodensitometer of conventional type which is modified so as to permit the practical application of the invention. The modification consists first in replacing the one-dimensional detector of this apparatus by a detector of the 2D type. This 2D detector can be a silicon detector or possibly a luminance intensifier screen.

All modern tomodensitometers make it possible to obtain images of oblique cross-sections. To this end, a vertical ring containing the source-detector unit which is capable of rotating about the patient during acquisition of the different views can be tilted either forward or backward through an angle of a few degrees. In order to carry out the invention with an apparatus of this type, it is only necessary for example to acquire two views whilst the ring is in the rearwardly tilted position. In this condition, the two views have orientations 5 and 8 and, in the case of these two views, an x-ray source would be located, for example, in positions 19 and 20 respectively. Once these two views have been acquired, it is only necessary to tilt the ring forward and to acquire a third view in a direction 11 whilst the x-ray source is in position 21. By passing from fifteen degrees to the rear to fifteen degrees to the front, the angle of tilt is of the order of 30°. This already permits a substantially "orthogonal" scan of the structure to be examined if this latter is placed in collinear relation to the axis 10 of the machine.

The console 22 of this machine includes all the computer and memory means for carrying out the programs 12 and 14 for reconstruction and visual display of the structures reconstructed on the screen 15.

An algebraic reconstruction algorithm of the iterative type has been describe-d for the first time in "Image reconstructions from projections", G. T. Herman, Academic Press, 1980. An improvement in this algorithm has also been proposed by K. M. Hanson-and G. W. Wecksung in "Local basis - functions approach to computed tomography", Applied Optics, Vol. 24, No. 23, December 1985, pages 4028–4039. The application of these algorithms to the radiological data acquired in accordance with the invention is immediate since the geometry of the projection-irradiation assembly is known each time. The algebraic reconstruction technique, as is known in the $$a_k(x, t, z) = x + \frac{z - \langle t, x \rangle}{\langle t, t \rangle} t \quad \text{if } \langle t, t \rangle \neq 0,$$
$$= x \quad \text{if } \langle t, t \rangle = 0.$$

This equation provides the sequence of functions $a_0$, $a_1, a_2$, etc., and also a way of choosing the $a_k$'s for any J-dimensional vectors x and t and for any real number z. The k's represent iterative steps which are described by the function $a_k$. The $\langle , \rangle$ denotes the inner product to two J-dimensional vectors. In order to practice the reconstruction techniques, it is necessary to compute the small $r_{ik}$ which appear in the equation $$y_{ik} = \sum_{j=1}^{J} r_{ik,j} x_j^{(k+1)};$$

When two dimensions are considered, $r_{ij}$ is equal to the length of the intersection between ray and pixel j where i goes from 1 to 256 cell 1D-detector, and where j goes from 1 to $256^2$ for a $256 \times 256$ pixel image.

For three dimension $r_{ij}$ is equal to the length of the intersection between ray i and voxel j, where i goes 1 to $256^2$ for a $256^2$ cell 2D-detector, and where j goes from 1 to $256^3$ for a 256x, 256x voxel image.

In either of the case or three dimensional operation, as is known in geometry, the computation of $r_{ij}$ is made without difficulty.

A program 12 which operates computer 6 as shown in FIG. 1 would be a known program wherein $r_{ij}$ variables are defined as the length of the intersection between a ray i and voxel j. As indicated in the above-referenced article to Hansen, because only two percent of the $r_{ij}$ elements are non-zero, the computations are simplified.

What is claimed is:

1. A method for acquisition of radiological data relating to a body irradiated with x-rays and for reconstruction of images of structures corresponding to said body in order to display said images of said structures, wherein, for the purpose of acquisition, said method comprises the steps of:
   a) directing a flux of x-rays to the body by means of a transmitter, said flux having a principal direction of irradiation with regard to said body,
   b) detecting a first view relating to a first given orientation of the principal direction with respect to the body by means of a two dimensional detector which is maintained opposite to the transmitter, said first view being constituted by a collection of data which are a function of the coordinates of loci on said detector and a function of the attenuation within the body of that portion of the x-rays which terminates at said loci,
   c) reiterating, prior to reconstruction, the preceding steps a) and b) for second and third principal directions, for producing second and third collections of data, said first, second, and third directions oriented so that a plane formed by any two of said directions, intersects the remaining principal direction,
   d) and wherein, for the purpose of reconstruction, an algebraic reconstuction algorithm is employed utilizing said first, second, and third collections of data to reconstruct one image.

2. The method as defined in claim 1, wherein said flux of x-rays directed to the body is continuous.

3. The method as defined in claim 1, further comprising the step of storing the first, second, and third collections of data in memory.

4. The method as defined in claim 1, further comprising the steps of extracting from the reconstruction, images of cross sections of the structures contained in said body and displaying said images on a monitor.

5. A method for acquisition of radiological data relating to a body irradiated with x-rays and for reconstruction of images of structures corresponding to said body in order to display said images of said structures, wherein, for the purpose of acquisition, said method comprises the steps of:
   a) directing a flux of x-rays to the body by means of a transmitter, said flux having a principal direction of irradiation with regard to said body,
   b) detecting a first view relating to a first given orientation of the principal direction with respect to the body by means of a two dimensional detector which is maintained opposite to the transmitter, said first view being constituted by a collection of data which are a function of the coordinates of loci on said detector and a function of the attenuation within the body of that portion of the x-rays which terminates at said loci,
   c) reiterating, prior to reconstruction, the preceding steps a) and b) for second and third principal directions, for producing second and third collections of data, said first, second, and third directions oriented so that a plane formed by any two of said directions intersects the remaining principal direction, said plane formed by any two of said principal directions being substantially at right angles to said remaining principal direction, d) and wherein, for the purpose of reconstruction, an algebraic reconstruction algorithm is employed utilizing said first, second, and third collections of data.

6. A method for acquisition of radiological data relating to a body irradiated with x-rays and for reconstruction of images of structures corresponding to said body in order to display said images of said structures, wherein, for the purpose of acquisition, said method comprises the steps of:
   a) directing a flux of x-rays to the body by means of a transmitter, said flux having a principal direction of irradiation with regard to said body,
   b) detecting a first view relating to a first given orientation of the principal direction with respect to the body by means of a two dimensional detector which is maintained opposite to the transmitter, said first view being constituted by a collection of data which are a function of the coordinates of loci on said detector and a function of the attenuation within the body of that portion of the x-rays which terminates at said loci,
   c) reiterating, prior to reconstruction, the preceding steps a) and b) for the second and third principal directions, said second and third principal directions having different relative orientations with respect to said body, and for producing second and third collection of data, said first, second, and third principal directions oriented so that they are orthogonal to each other,
   d) reconstructing at least one image from said first, second, and third collections of data using an algebraic reconstruction algorithm.

7. The method as defined in claim 6, wherein said flux of x-rays directed to the body is continuous.

8. The method as defined in claim 6, further comprising the step of storing the first, second, and third connections of data in memory.

9. The method as defined in claim 6, further comprising the steps of extracting from the at least one reconstructed image, an image of a cross-section of the structures contained in said body and displaying said image on a monitor.

10. A method for acquisition of radiological data relating to a body irradiated with x-rays and for reconstruction of images of structures corresponding to said body in order to display said images of said structures, wherein, for the purpose of acquisition, said method comprises the steps of:
   a) directing a flux of x-rays to the body by means of a transmitter, said flux having a principal direction of irradiation with regard to said body,
   b) detecting a first view relating to a first given orientation of the principal direction with respect to the body by means of a two dimensional detector which is maintained opposite to the transmitter, said first view being constituted by a collection of data which are a function of the coordinates of loci on said detector and a function of the attenuation within the body of that portion of the x-rays which terminates at said loci,
   c) reiterating, prior to reconstruction, the preceding steps a) and b) for second and third principal directions, said second and third principal directions lying in a plane which is perpendicular to said first principal direction, and for producing second and third collections of data;
   d) reconstructing at least one image from said first, second, and third collections of data using an algebraic reconstruction algorithm.

11. The method as defined in claim 10, wherein said flux of x-rays directed to the body is continuous.

12. The method as defined in claim 10, further comprising the step of storing the first, second, and third collections of data in memory.

13. The method as defined in claim 10, further comprising the steps of extracting from the at last one reconstructed image, an image of a cross-section of the structures contained in said body and displaying said image on a monitor.

* * * * *